United States Patent
Mendenhall et al.

(10) Patent No.: US 10,934,561 B1
(45) Date of Patent: Mar. 2, 2021

(54) METHODS AND PRODUCTS FOR INCREASING CFTR

(71) Applicants: Eric Matthew Mendenhall, Madison, AL (US); Candice Joyce Coppola, Huntsville, AL (US)

(72) Inventors: Eric Matthew Mendenhall, Madison, AL (US); Candice Joyce Coppola, Huntsville, AL (US)

(73) Assignee: Board of Trustees of the University of Alabama, for and on behalf of the University of Alabama in Huntsville, Huntsville, AL (US)

(*) Notice: Subject to any disclaimer, the term of this patent is extended or adjusted under 35 U.S.C. 154(b) by 43 days.

(21) Appl. No.: 15/796,414

(22) Filed: Oct. 27, 2017

Related U.S. Application Data

(60) Provisional application No. 62/413,777, filed on Oct. 27, 2016.

(51) Int. Cl.
| | |
|---|---|
| *A61P 11/00* | (2006.01) |
| *C07K 14/195* | (2006.01) |
| *C07K 14/01* | (2006.01) |
| *C07K 14/005* | (2006.01) |
| *C12N 15/11* | (2006.01) |
| *C12N 7/00* | (2006.01) |
| *C12N 15/90* | (2006.01) |
| *C12N 15/63* | (2006.01) |
| *C12N 15/10* | (2006.01) |
| *C12N 9/22* | (2006.01) |

(52) U.S. Cl.
CPC .......... *C12N 15/907* (2013.01); *C12N 9/22* (2013.01); *C12N 15/1024* (2013.01); *C12N 15/63* (2013.01); *C12N 2310/20* (2017.05)

(58) Field of Classification Search
None
See application file for complete search history.

(56) References Cited

PUBLICATIONS

Mendenhall, et al. (Sep. 21, 2016) "Increasing CFTR Gene Expression Using Synthetic Transcriptional Activators", Pediatric Pulmonology, Poster Session Abstract 146, vol. 51, Issue S45 (Supplement: the 30th Annual North American Cystic Fibrosis Conference, Orange County Convention Center, Orlando, FL), p. 247.*
Senis, et al. (2014) "CRISPR/Cas9-mediated genome engineering: An adeno-associated viral (AAV) vector toolbox", Biotechnology Journal, 9: 1402-12.*
Uhlmann, et al. (2014) "The VP16 Activation Domain Establishes an Active Mediator Lacking CDK8 in Vivo", The Journal of Biological Chemistry, 282(4): 2163-73.*
Marle, et al. (2015) "The New State of the Art: Cas9 for Gene Activation and Repression", Molecular and Cellular Biology, 35(22): 3800-09.*
Quon (2016) "New and emerging targeted therapies for cystic fibrosis", The BMJ, 352: article i859 (Printed as 30 pages from web).*
Nagayama, et al. (1999) "Characterization of CFTR expression in a human pulmonary mucoepidermoid carcinoma cell line, NCI-H292", FEBS Letters, 455: 215-18.*
Viart, et al. (2012) "Functional Analysis of a promoter variant identified in the CFTR gene in cis of a frameshift mutation", European Journal of Human Genetics, 20(2): 180-84.*
Quiton PM, Physiological Basis of Cystic Fibrosis: A Historical Perspective, Physiol Rev. Jan. 1999;79(1 Suppl):S3-S22.
Stevens DP & Marshall BC, Healthcare improvement is incomplete until it is published: the cystic fibrosis initiative to support scholarly publication, BMJ Qual Saf 2014;23;i104-i107.
Mali P, et al., Cas9 as a versatile tool for engineering biology, Nat Methods Oct. 2013;10(10):957-63.

* cited by examiner

*Primary Examiner* — Robert M Kelly
(74) *Attorney, Agent, or Firm* — Maynard Cooper & Gale, P. C.; Jon E. Holland

(57) ABSTRACT

Cystic Fibrosis (CF) is a recessive, lethal genetic disease in which many patients have inherited DNA mutations that create a CFTR protein that is produced, but ineffective in its function. The present disclosure generally pertains to methods and products for increasing CFTR production through the use of a CRISPR/dCas9 system. This disclosure describes such system, which comprises gRNA configured to target the CFTR domain and dCas9 configured to upregulate expression of the gRNA target, and methods of using the same.

24 Claims, 4 Drawing Sheets
Specification includes a Sequence Listing.

METHODS AND PRODUCTS FOR INCREASING CFTR

CROSS REFERENCE TO RELATED APPLICATION

This application claims priority to U.S. Provisional Patent Application No. 62/413,777, entitled "Methods and Products for Increasing CFTR" and filed on Oct. 27, 2016, which is incorporated herein by reference.

BACKGROUND OF THE INVENTION

Cystic Fibrosis (CF) is a recessive, lethal genetic disease affecting approximately one in every 3500 births in the United States. More than ten million Americans are carriers of CF, and approximately 30,000 have been diagnosed with CF, with about 1,000 new cases diagnosed each year [Quiton P M, Physiol Rev. 1999 January; 79(1 Suppl):53-522]. Notable symptoms of CF include chronic pulmonary disease (the primary cause of morbidity and mortality), pancreatic exocrine insufficiency, male infertility, and elevated electrolyte levels in perspiration, ultimately causing thick, sticky mucus to form in the lungs, pancreas, and other organs. Despite significant advances in treatment during the past few decades, the median predicted age of survival as of 2012 was just 41.1 years [Stevens DP & Marshall BC, BMJ Qual Saf 2014; 23].

The majority of CF patients have inherited DNA mutations to their cystic fibrosis transmembrane conductance regulator (CFTR) gene that results in a CFTR protein that is produced, but ineffective in its function. CF is observed to be a highly variable disease. There are over 1,000 different types of CFTR mutations with varying level of CFTR function. One source of clinical variability, for example, are mutations that reduce or eliminate CFTR at the cell surface (such as ΔF508), which tend to lead to more severe phenotypes than mutations that lessen CFTR function without significantly affecting quantity. Even within a given genotype, however, there is significant variation in individual disease progression, and the source of this variation remains unknown. Years of research has produced pharmaceuticals that assist the effectiveness of these partially functional CFTR proteins, often alleviating some or most of the clinical symptoms of CF. Most patients with mutations to CFTR, when following a regimen of currently available pharmaceuticals, however, still lack enough CFTR protein function to significantly alleviate clinical symptoms of CF.

As disclosed herein, methods that increase activation of the CFTR gene to cause the production of more CFTR protein, either alone or in combination with pharmacological agents, may cause CF disease symptoms to be reduced. To potentially uncover methods of producing more CFTR protein, the present disclosure provides methods to upregulate CFTR at the level of transcription.

SUMMARY OF THE INVENTION

In certain embodiments, the present disclosure pertains to a method of increasing the level of CFTR production in a cell, comprising the steps of: delivering dCas9 and gRNA to the cell; wherein the gRNA includes a targeting region designed to target the CFTR promoter; and wherein the dCas9 is configured to recognize a protospacer adjacent motif sequence (PAM), bind DNA and upregulate expression of the gRNA target. In certain embodiments, the dCas9 and gRNA are delivered and encoded by viral vector, which may include, but is not limited to, adeno-associated virus (AAV) and lentiviral vectors. In certain embodiments, the dCas9 and gRNA are delivered by nanoparticles. In certain embodiments, the gRNA is encoded by the sequence comprising SEQ ID NO. 2. In certain embodiments, the CFTR promoter is encoded by the sequence comprising SEQ ID NO. 1. In certain embodiments, the dCas9 comprises a fusion protein comprising at least one of the group consisting of VP16, VP64, p65, HSF1, p300 and RTA. In certain embodiments the gRNA contains an MS2 nucleic acid sequence which is capable of binding to an MS2 polypeptide, which is fused to activators such as SAM or VPR. In certain embodiments, the dCas9 polypeptide sequence is derived from *Streptococcus pyogenes, Streptococcus thermophiles* or *Neisseria meningitides*.

In certain embodiments, the present disclosure pertains to a method of increasing the level of CFTR production in a subject, comprising the steps of: delivering dCas9 and gRNA to at least one cell in the subject; wherein the gRNA includes a targeting region designed to target a CFTR promoter; and wherein the dCas9 is configured to upregulate expression of the gRNA target. In certain embodiments, the method further comprises administering at least one CFTR modulating drug to the subject. In certain embodiments, the dCas9 and gRNA are delivered and encoded by viral vector, which may include, but is not limited to, adeno-associated virus (AAV) and lentiviral vectors. In certain embodiments, the dCas9 and gRNA are encapsulated and delivered by cationic liposome. In certain embodiments, the gRNA is encoded by the sequence comprising SEQ ID NO. 2. In certain embodiments, the CFTR promoter is encoded by the sequence comprising SEQ ID NO. 1. In certain embodiments, the dCas9 comprises a fusion protein comprising at least one of the group consisting of VP16, VP64, p65, HSF1, p300 and RTA. In certain embodiments, the dCas9 comprises SAM or VPR. In certain embodiments, the dCas9 polypeptide sequence is derived from *Streptococcus pyogenes, Streptococcus thermophiles* or *Neisseria meningitides*.

In certain embodiments, the present disclosure pertains to a CRISPR-Cas system, comprising: a dCas9 protein; and a gRNA comprising a targeting region designed to target a CFTR promoter; and whereby the dCas9 is configured to upregulate expression of the gRNA target. In certain embodiments, the dCas9 and gRNA are delivered and encoded by viral vector, which may include, but is not limited to, adeno-associated virus (AAV) and lentiviral vectors. In certain embodiments, the gRNA is encoded by the sequence comprising SEQ ID NO. 2. In certain embodiments, the CFTR promoter is encoded by the sequence comprising SEQ ID NO. 1. In certain embodiments, the dCas9 comprises a fusion protein comprising at least one of the group consisting of VP16, VP64, p65, HSF1, p300 and RTA. In certain embodiments, the dCas9 comprises SAM or VPR. In certain embodiments, the dCas9 polypeptide sequence is derived from *Streptococcus pyogenes, Streptococcus thermophiles* or *Neisseria meningitides*.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
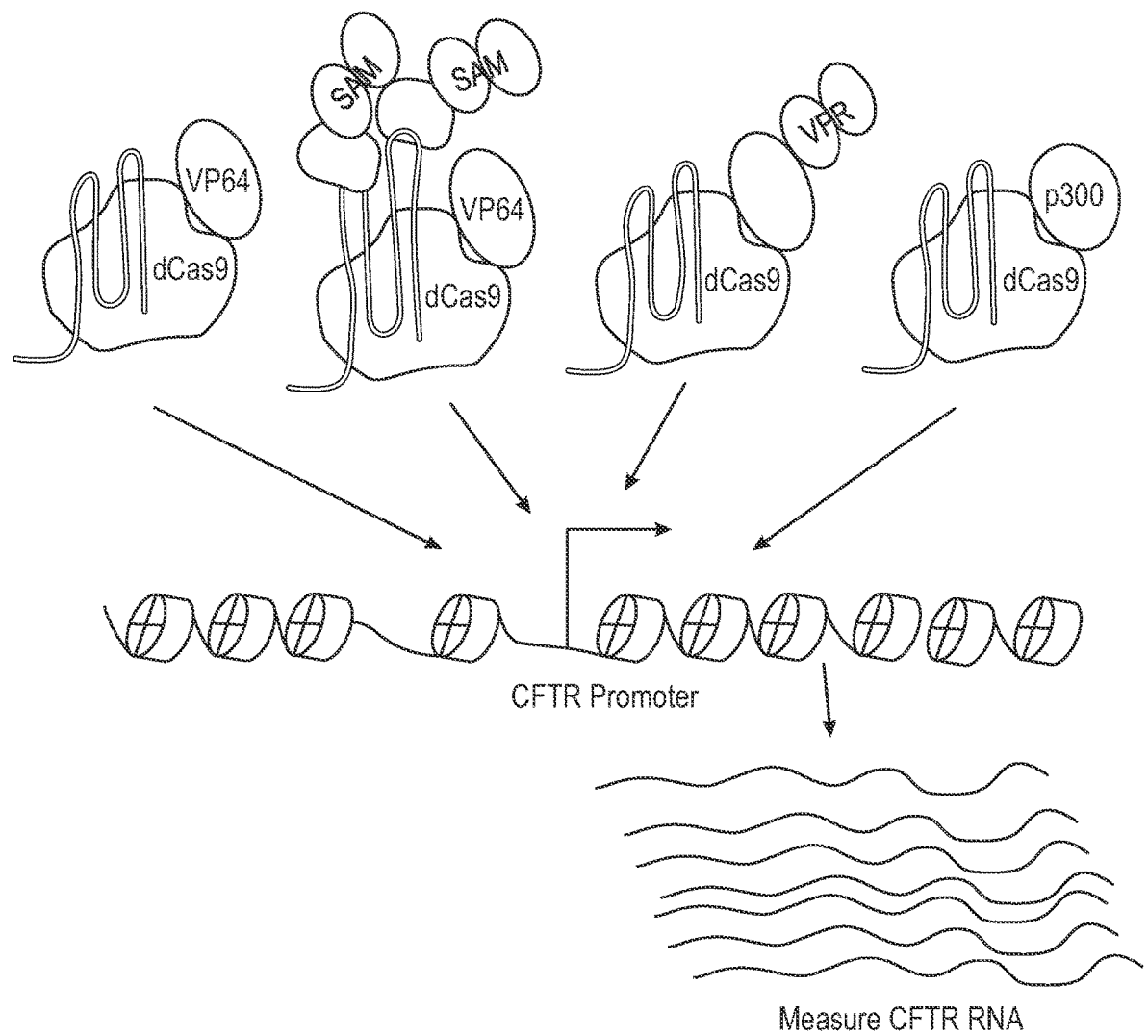
FIG. 1 is an illustration depicting four versions of catalytically inactive Cas9 (dCas9) used to directly or indirectly bring various transcriptional activating proteins to the CFTR promoter and potentially increase the amount of CFTR RNA being produced.

Cystic Fibrosis (CF) is a recessive, lethal genetic disease in which many patients have inherited DNA mutations that create a CFTR protein that is produced, but at insufficient levels and/or ineffective in its function. The present disclosure generally pertains to methods and products for increasing CFTR production through the use of a CRISPR/dCas9 system. This disclosure describes such system, which comprises gRNA configured to target the CFTR domain and dCas9 configured to upregulate expression of the gRNA target, and methods of using the same.

As used herein, "Cas9" means non-specific CRISPR-associated endonuclease. "dCas9" means "dead" Cas9 that is not configured to cleave target DNA.

As used herein, "CRISPR" means Clustered Regularly Interspaced Short Palindromic Repeats.

As used herein, "gRNA" means guide RNA and is a short synthetic RNA composed of a "scaffold" sequence necessary for Cas9-binding and a user-defined nucleotide "spacer" or "targeting" sequence of approximately 20 nucleotides in length that defines the genomic target.

As used herein, "SAM" means CRISPR/Cas9 Synergistic Activation Mediator and comprises a VP64 fusion to dCas9 and gRNA containing MS2 RNA loops in the presence of an MS2-p65-HSF1 fusion protein.

As used herein, "subject" means a human at risk of, suspected of having, or diagnosed with Cystic Fibrosis.

As used herein, "VPR" means a direct fusion of VP64, p65 and Rta to dCas9 protein.

CRISPR/dCas9 is a tool that originates from bacteria in what is typically described as a bacterial immune system. CRISPRs are DNA loci that contain short repetitions of base sequences. Each such repetition is followed by short segments of "spacer" DNA from the bacteria's previous exposure to foreign genetic elements. The CRISPR spacers recognize and silence the foreign genetic in a manner somewhat similar to RNAi in eukaryotes. In short, CRISPR/Cas9 consists of a gRNA and a non-specific endonuclease, Cas9. gRNA is a short, synthetic RNA which includes a sequence configured to bind to Cas9 and a separate targeting sequence configured to target a genomic target, allowing genomic engineering [see, e.g., Mali P, et al. Nat Methods. 2013 Oct; 10(10):957-63].

Conventional CRISPR/Cas9 has been used to knock-out target genes. Here, however, the applicants employ a modified CRISPR/Cas9 system designed to enhance activation of a CFTR target. Specifically, the present disclosure contemplates the use of "dead" Cas9, or dCas9, which has been modified to lack the ability to cleave DNA while retaining its ability to bind a target based on the gRNA sequence. Such modification of dCas9 can be achieved by point mutations. In certain embodiments, the dCas9 polypeptide sequence is derived from *Streptococcus pyogenes, Streptococcus thermophiles* or *Neisseria meningitides*.

dCas9 may be complexed with one or more activators to thereby enhance activation of a target based on the gRNA. dCas9 may be configured to upregulate expression of a gRNA target in several ways. For example, the dCas9 may comprise SAM, VPR, VP64, or p300, each of which is a transcriptional activator. SAM, for example, is a VP64 fusion to dCas9 and gRNA containing MS2 RNA loops in the presence of an MS2-p65-HSF1 fusion protein.

In certain embodiments, the present disclosure pertains to a method of increasing the level of CFTR production in a cell, comprising the steps of: delivering dCas9 and gRNA to the cell; wherein the gRNA includes a targeting region designed to target a CFTR promoter; and wherein the dCas9 is configured to upregulate expression of the gRNA target. Suitable cells include vertebrate cells that express CFTR, including, but not limited to, A549 and Calu3 lung cell lines, human bronchial epithelial (HBE) cells, and CAPAN-1 pancreatic cells.

dCas9 and gRNA may be delivered to a cell in several ways, including, but not limited to, viral vectors (which may encode dCas9 and/or gRNA), electroporation, cationic liposomes, cationic polymers, cell-penetrating peptides (CPP), and/or nanoparticle-based delivery. Viral vectors may include, but are not limited to, adeno-associated virus (AAV), lentivirus, adenovirus and retrovirus vectors, which may enter cells via receptor-mediated endocytosis, resulting in expression of genes from the vector. In contrast to retrovirus, adenoviral infection of the cells does not result in chromosomal integration because adenoviral DNA can replicate episomally.

Alternatively, dCas9 and gRNA may be encapsulated in cationic liposomes and delivered to target cells. Cationic polymers include, but are not limited to, polyethyleneimine (PEI) and other polymers known in the art. Cell-penetrating peptides may be complexed to gRNA to form condensed, positively-charged nanoparticles and may be fused to dCas9 using thioether bonds. Nanoparticle-based delivery includes, but is not limited to, lipid nanoparticle-mediated delivery. dCas9 and gRNA may be delivered by separate delivery methods. The selection of delivery method may be used to determine the duration of activity within the target cells; delivery by viral vector may be used for long-term action, whereas lipid nanoparticle delivery may be used for short-term action, for example due to degradation of messenger RNA within a period of a few days.

The gRNA may be configured to target the CFTR promoter domain. For example, gRNA may be encoded by the sequence comprising SEQ ID NO. 2, SEQ ID NO. 3, SEQ ID NO. 4 or other sequence complementary to a CFTR target promoter domain. The CFTR domain may comprise a CFTR promoter sequence, for example, the sequence comprising SEQ ID NO. 1.

In certain embodiments, the present disclosure pertains to a method of increasing the level of CFTR production in a subject, comprising the steps of: delivering dCas9 and gRNA to at least one cell in the subject; wherein the gRNA includes a targeting region designed to target a CFTR promoter; and wherein the dCas9 is configured to upregulate expression of the gRNA target, for example by attaching one or more transcriptional activators to dCas9.

dCas9 and gRNA may be delivered to at least one cell in a subject in several ways, including, but not limited to, viral vectors, electroporation, cationic liposomes, cationic polymers, cell-penetrating peptides (CPP), and/or nanoparticle-based delivery, as described above. Each deliverable composition is prepared in a manner rendering it free of impurities that would otherwise potentially harm the subject and in a carrier suitable for the method of administration (e.g., intravenous injection), as known in the art. Viral vectors, cationic liposomes and nanoparticles may be delivered by: injection, including, but not limited to, intravenous injection or injection directly into the target tissue of the subject; or by nebulization and inhalation by the subject.

In certain embodiments, the method further comprises administering at least one CFTR modulator drug to the subject. CFTR modulator drugs are known in the art and include, but are not limited to, Ivacaftor, Lumacaftor (VX-809), VX-661, Ataluren (PTC124), sodium 4-phenylbutarate (4PBA), VRT-532 and N6022.

In certain embodiments, the present disclosure pertains to a CRISPR-dCas9 system, comprising: a dCas9 protein; and a gRNA comprising a targeting region designed to target a CFTR promoter; and whereby the dCas9 is configured to upregulate expression of the gRNA target. In certain embodiments, the dCas9 and gRNA are delivered and encoded by viral vector, which may include, but is not limited to, adeno-associated virus (AAV) and lentiviral vectors. In certain embodiments, the gRNA is encoded by the sequence comprising SEQ ID NO. 2. In certain embodiments, the CFTR promoter is encoded by the sequence comprising SEQ ID NO. 1. In certain embodiments, the dCas9 comprises a transcriptional activator, for example SAM, VPR, VP64 or p300.

The CRISPR-dCas9 system described in paragraph [0028] may be prepared as a formulation using methods known or hereafter developed in the art of pharmacology. In general, such preparatory methods include the step of bringing the active ingredient into association with an excipient, and then, if necessary and/or desirable, shaping and/or packaging the product into a desired single- or multi-dose unit.

EXAMPLES

Methods and products (CRISPR gRNAs, dCas9 fusions, and CFTR targeting systems) were developed by applicants for increasing CFTR RNA expression in a cell, as well as uses of these methods for the treatment of CF in subjects. Applicants utilized a variety of methods, including dCas9 based methods, to efficiently target the CFTR promoter to increase CFTR RNA expression almost 200 fold versus control in lung cell lines. Induction of CFTR was tested using A549 cells, and subsequently Calu3 cells. Five distinct methods of upregulating CFTR were tested using quantitative RT-PCR with SDHA and TBP as the internal controls. These five methods include VP64, VPR, SAM and p300 as well as a protein based delivery of VP64 (FIG. 1). SAM uses VP64 fusion to cCas9 along with the gRNA containing MS2 RNA loops in the presence of an MS2-p65-HSF1 fusion protein. VPR is a direct fusion of VP64, p65 and Rta to the dCas9 protein.

Figure 2:
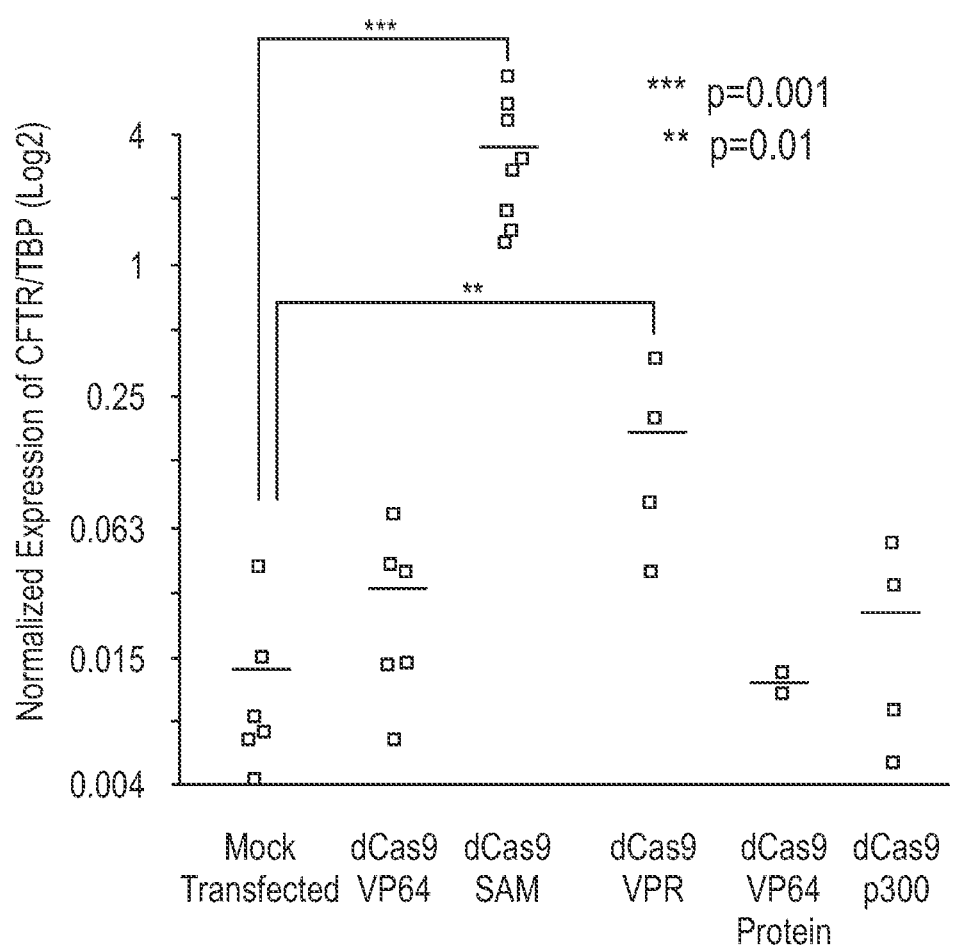
FIG. 2 is a chart showing the upregulation of CFTR using four strategies (from FIG. 1) tested with the same gRNA in A549 lung epithelial cells. All four strategies induced upregulation of CFTR, with SAM and VPR showing significant upregulation (unpaired t-test). CFTR expression was calculated using qPCR and all data were normalized to a housekeeping gene (SDHA). CFTR expression was calculated as a ratio to another housekeeping gene (TBP). All data are shown on a Log 2 scale.

The applicants used A549 cells due to prior success delivering epigenome editing reagents including DNA and proteins. The applicants demonstrated that the SAM method was the best at upregulating CFTR, but VPR also significantly increased CFTR expression (FIG. 2). VP64 (delivered as both DNA and protein form) and p300 showed little increase in CFTR expression. These fusions, however, could show better increase in other cell types or genomic locations around CFTR. Further, the modest increase in expression shown could actually be physiologically relevant in certain scenarios, such as hypomorph genotypes or in subjects treated with CFTR modulator drugs.

Figure 3:
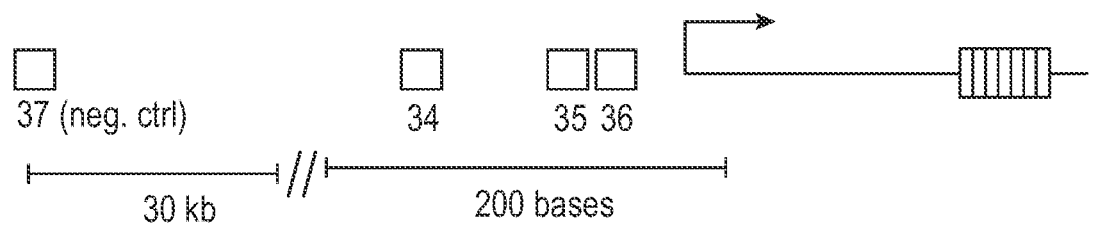
FIG. 3 is an illustration depicting alternative gRNAs designed around the CFTR promoter to optimize CFTR upregulation with the dCas9:SAM method. A negative control gRNA (encoded by the sequence comprising SEQ ID NO. 5) was designed 30 kb away from the CFTR promoter.
Figure 4:
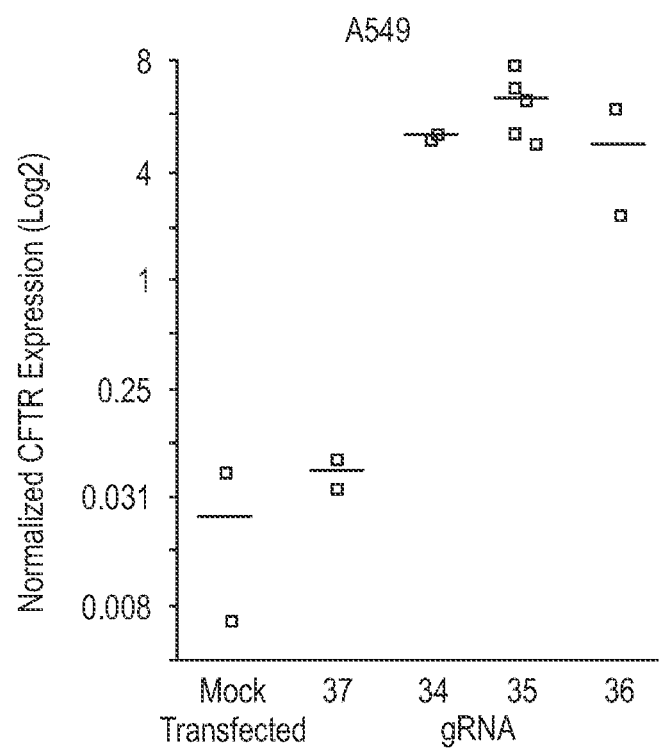
FIG. 4 is a chart showing normalized CFTR expression using dCas9:SAM with four different gRNAs in two different epithelial cell lines. Data were normalized as in FIG. 2. Significantly higher endogenous CFTR expression was observed in the Calu3 cell line.
Figure 4:
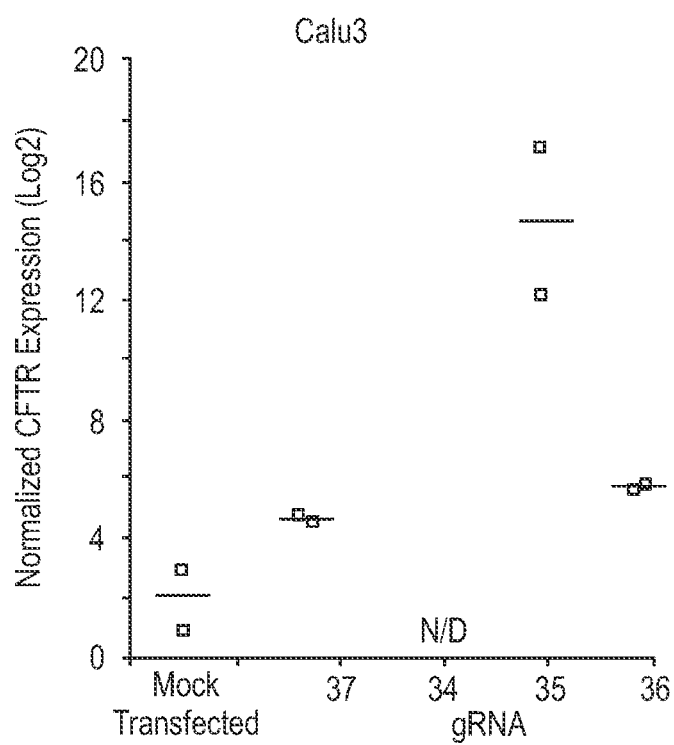

The applicants next determined if a tunable activation could be achieved by altering the targeting, or position, of the guide RNA (gRNA) in the CFTR promoter (FIG. 3 and Table 1, below). Using the SAM method, two additional gRNAs, as well as a negative control located 30 kilobases away, were tested. Also tested was Calu3, a lung epithelial cell line which has significantly higher expression of CFTR compared with A549 cells. gRNA 35 (used to obtain the results in FIG. 2) showed the highest upregulation of CFTR in both A549 and Calu3 cells, while the negative control gRNA showed no significant upregulation of CFTR (FIG. 4).

TABLE 1

Sequence of DNA CFTR Promoter and gRNA targets tested

| | |
|---|---|
| 2500 bp sequence classified as the "CFTR promoter" (SEQ ID NO. 1) | TAACAAAGAAGAACTAATTATTAATTTATTTCAAA ATGCATGTATTATATTTGATGGGCCACACTAACAG TTATAAACCAAACAACAGATTGGGAATGGGGAAG TGGATGTGGTGAGTTCAATCACATGTCTGGGAAA AGTCAATAGTGAAGACAGAGTCTCACAATTTTTTG TCATAATGGAGAGATGAAAACACAGGTAGAGGAT TTCAAACAACAGAGTGGATGGTGAGTTAAAAATG CTGAAATTCTTTCCTGGTGTCTAACTTAATGCAAT GTGGTTTATCTCTTTGCTCTTTTCTCTACTATTCAA ATTTAGGATAATAAAGATTAAATGTTTCTAAATCT TACTTTACAATATCAAGAAAAAAAGGTATGCTTTT GCCCACGGAAGGGCAAAGCAGAGCTATGAAAACC TGCTGAACACATTCTTTATTTTCAACACAGGTTCT TGTCTTTCCATCATGAAATGCACATTTTATTTGTAC TGTATTTGGGTGACCACAAGTCAACAACAAGATA ATTCACAAGACCCTTGCCTTAGATGTGTCGGCAAT AAAGTAATCAGGCCAAAATTTTTACTTTCCTTTGA ATTTTTCAATTCAAACACAATGTATGCTTGCTTTT ACACCAGTAGGGTTVAGGGATTAGAGGGTTGGCTC TTTAAAAACCGTCAGAGACACAGGCAATCCTACA CAAAATTCTCAGAAGGAAGGCGCCTACGCCTGGG AATGCCCAGATGCCCCTCAGAGAGTTGAAGATGG CGTTTCTCTGAGTCAGGTCAAAGTTAACACATTAC CTTCGCTTCAAAGACTGCTTGGCTTCCTTTCGGTG GATTAGTCAAGATGTTTTGCTGACTGAGACTAGGA AATCTATAGGAGGGCGGGTTAGTTTACATTGTTCC TTGTCATTATCGCTAAAACACTCCAAAGCCTTCCT TAAAAATGCGCACTGGGCTAAAAAGGATAGACAA GGAACACATCCTGGGCCGGTAATTACGCAAAGCA TTATCTCCTCTTACCTCCTTGCAGATTTTTTTTTCT CTTTCAGTACGTGTCCTAAGATTTCTGTGCCACCC TTGGAGTTCACTCACCTAAACCTGAAACTAATAAA GCTTGGTTCTTTTCTCCGACACGCAAAGGAAGCGC TAAGGTAAATGCATCAGACCCACACTGCCGCGGA ACTTTTCGGCTCTCTAAGGCTGTATTTTGATATAC GAAAGGCACATTTTCCTTCCCTTTTCAAAATGCAC CTTGCAAACGTAACAGGAACCCGACTAGGATCAT CGGGAAAAGGAGGAGGAGGAGGAAGGCAGGCTC CGGGGAAGCTGGTGGCAGCGGGTCCTGGGTCTGG CGGACCCTGACGCGAAGGAGGGTCTAGGAAGCTC TCCGGGGAGCCGGTTCTCCCGCCGGTGGCTTCTTC TGTCCTCCAGCGTTGCCAACTGGACCTAAAGAGA |

TABLE 1-continued

Sequence of DNA CFTR Promoter and gRNA targets tested

```
              GGCCGCGACTGTCGCCCACCTGCGGGATGGGCCT
              GGTGCTGGGCGGTAAGGACACGGACCTGGAAGGA
              GCGCGCGCGAGGGAGGGAGGCTGGGAGTCAGAA
              TCGGGAAAGGGAGGTGCGGGCGGCGAGGGAGC
              GAAGGAGGAGAGGAGGAAGGAGCGGGAGGGGTG
              CTGGCGGGGGTGCGTAGTGGGTGGAGAAAGCCGC
              TAGAGCAAATTTGGGGCCGGACCAGGCAGCACTC
              GGCTTTTAACCTGGGCAGTGAAGGCGGGGGAAAG
              AGCAAAAGGAAGGGGTGGTGTGCGGAGTAGGGG
              TGGGTGGGGGGAATTGGAAGCAAATGACATCACA
              GCAGGTCAGAGAAAAAGGGTTGAGCGGCAGGCA
              CCCAGAGTAGTAGGTCTTTGGCATTAGGAGCTTGA
              GCCCAGACGGCCCTAGCAGGGACCCCAGCGCCCG
              AGAGACCATGCAGAGGTCGCCTCTGGAAAAGGCC
              AGCGTTGTCTCCAAACTTTTTTTCAGGTGAGAAGG
              TGGCCAACCGAGCTTCGGAAAGACACGTGCCCAC
              GAAAGAGGAGGGCGTGTGTATGGGTTGGGTTTGG
              GGTAAAGGAATAAGCAGTTTTTAAAAAGATGCGC
              TATCATTCATTGTTTTGAAAGAAAATGTGGGTATT
              GTAGAATAAAACAGAAAGCATTAAGAAGAGATG
              GAAGAATGAACTGAAGCTGATTGAATAGAGAGCC
              ACATCTACTTGCAACTGAAAAGTTAGAATCTCAA
              GACTCAAGTACGCTACTATGCACTTGTTTTATTTC
              ATTTTTCTAAGAAACTAAAAATACTTGTTAATAAG
              TACCTAAGTATGGTTTATTGGTTTTCCCCCTTCATG
              CCTTGGACACTTGATTGTCTTCTTGGCACATACAG
              GTGCCATGCCTGCATATAGTAAGTGCTCAGAAAA
              CATTTCTTGACTGAATTCAGCCAACAAAAATTTTG
              GGGTAGGTAGAAAATATATGCTTAAAGTATTTATT
              GTTATGAGACTGGATATATCTAGTATTTGTCACAG
              GTAAATGATTCTTCAAAAATT
CFTR gRNA 34  GGCGGGGGTGCGTAGTGGG
(SEQ ID NO. 2)

CFTR gRNA 35  GCCTGGGCAGTGAAGGCGG
(SEQ ID NO. 3)

CFTR gRNA 36  GAAAGAGCAAAAGGAAGGGG
(SEQ ID NO. 4)

CFTR gRNA     GTAAAGGTACAAAACTTAC
Negative
Control
(SEQ ID NO. 5)

CFTR nm gRNA  GGCCGGACCAGGCAGCACTCG
(SEQ ID NO. 6)
```

VP64, VPR, SAM or p300 may be utilized by expression in AAV and Lentiviral vectors for use in vivo and in vitro. Such vectors may result in the constitutive expression of VP64, VPR, SAM or p300R to upregulate CFTR long-term. Further, the addition of VP64, VPR, SAM or p300 constructs to primary epithelial cell lines (such as HBE cells) can increase CFTR and provide a useful resource for research purposes.

The methods and products disclosed herein for increasing production of CFTR in subjects with CF provide significant benefits compared with conventional treatment methods. Such methods and products enable target cells in the subject to dramatically increase production of CFTR; in vitro, this increase was approximately 200-fold relative to control. Given the lethal nature of CF, such dramatic increases in CFTR may result in significant clinical benefits to subjects with CF.

This application references various publications. The disclosures of these publications, in their entireties, are hereby incorporated by reference into this application to describe more fully the state of the art to which this application pertains. The references disclosed are also individually and specifically incorporated herein by reference for material contained within them that is discussed in the sentence in which the reference is relied on.

The methodologies and the various embodiments thereof described herein are exemplary. Various other embodiments of the methodologies described herein are possible.

---

Now, therefore, the following is claimed:

1. A method of increasing the level of CFTR production in a cell,
comprising the steps of:
delivering dCas9 and gRNA to the cell;
wherein the gRNA includes a targeting region designed to target a CFTR promoter; and
wherein the dCas9 is configured to upregulate expression of the gRNA target and wherein dCas9 comprises a fusion protein comprising at least one of the group consisting of VP16, VP64, p65, HSF1, p300 and RTA, such that upregulation of the gRNA target occurs and increases the level of CFTR production in the cell.

2. The method of claim 1, wherein at least one of dCas9 and gRNA is delivered and encoded by viral vector.

3. The method of claim 1, wherein at least one of dCas9 and gRNA is delivered by nanoparticles.

4. The method of claim 1, wherein the gRNA and dCas9 ribonucleoprotein complex comprises SAM.

5. The method of claim 1, wherein the dCas9 is selected from the group consisting of polypeptide sequences derived from *Streptococcus pyogenes, Streptococcus thermophiles* and *Neisseria meningitides*.

6. The method of claim 1, wherein the dCas9 comprises VPR.

7. The method of claim 1, wherein the gRNA is encoded by the sequence comprising SEQ ID NO. 2.

8. The method of claim 1, wherein the CFTR promoter is encoded by the sequence comprising SEQ ID NO. 1.

9. A method of increasing the level of CFTR production in a subject, comprising the steps of:
delivering dCas9 and gRNA to at least one cell in the subject;
wherein the gRNA includes a targeting region designed to target a CFTR promoter; and
wherein the dCas9 is configured to upregulate expression of the gRNA target and wherein dCas9 comprises a fusion protein comprising at least one of the group consisting of VP16, VP64, p65, HSF1, p300 and RTA, such that upregulation of the gRNA target occurs and increases the level of CFTR production in the subject.

10. The method of claim 9, wherein at least one of dCas9 and gRNA is delivered and encoded by viral vector.

11. The method of claim 9, wherein at least one of dCas9 and gRNA is delivered by liposomes.

12. The method of claim 9, wherein at least one of dCas9 and gRNA is nebulized prior to delivery to the subject.

13. The method of claim 9, wherein the gRNA and dCas9 ribonucleoprotein complex comprises SAM.

14. The method of claim 9, wherein the dCas9 is selected from the group consisting of polypeptide sequences derived from *Streptococcus pyogenes, Streptococcus thermophiles* and *Neisseria meningitides*.

15. The method of claim 9, wherein the dCas9 comprises VPR.

16. The method of claim 9, wherein the gRNA is encoded by the sequence comprising SEQ ID NO. 2.

17. The method of claim 9, wherein the CFTR promoter is encoded by the sequence comprising SEQ ID NO. 1.

18. The method of claim 9, further comprising the step of administering at least one CFTR modulator drug to the subject.

19. A CRISPR-Cas system comprising:
a dCas9 protein comprising a fusion protein comprising at least one of the group consisting of VP16, VP64, p65, HSF1, p300 and RTA; and
a gRNA comprising a targeting region designed to target a CFTR promoter;
whereby the dCas9 is configured to recognize a protospacer adjacent motif sequence, bind DNA and upregulate expression of the gRNA target.

20. The system of claim 19, wherein the gRNA and dCas9 ribonucleoprotein complex comprises SAM.

21. The system of claim 19, wherein the dCas9 is selected from the group consisting of polypeptide sequences derived from *Streptococcus pyogenes, Streptococcus thermophiles* and *Neisseria meningitides*.

22. The system of claim 19, wherein the dCas9 comprises VPR.

23. The system of claim 19, wherein the gRNA is encoded by the sequence comprising SEQ ID NO. 2.

24. The system of claim 19, wherein the CFTR promoter is encoded by the sequence comprising SEQ ID NO. 1.

* * * * *

SEQUENCE LISTING

<160> NUMBER OF SEQ ID NOS: 6

<210> SEQ ID NO 1
<211> LENGTH: 2500
<212> TYPE: DNA
<213> ORGANISM: Homo sapiens

<400> SEQUENCE: 1

```
taacaaagaa gaactaatta ttaatttatt tcaaaatgca tgtattatat ttgatgggcc      60
acactaacag ttataaacca aacaacagat tgggaatggg gaagtggatg tggtgagttc     120
aatcacatgt ctgggaaaag tcaatagtga agacagagtc tcacaatttt ttgtcataat     180
ggagagatga aaacacaggt agaggatttc aaacaacaga gtggatggtg agttaaaaat     240
gctgaaattc tttcctggtg tctaacttaa tgcaatgtgg tttatctctt tgctcttttc     300
tctactattc aaatttagga taataaagat taaatgtttc taaatcttac tttacaatat     360
caagaaaaaa aggtatgctt ttgcccacgg aagggcaaag cagagctatg aaaacctgct     420
gaacacattc tttattttca acacaggttc ttgtctttcc atcatgaaat gcacatttta     480
tttgtactgt atttgggtga ccacaagtca acaacaagat aattcacaag acccttgcct     540
tagatgtgtc ggcaataaag taatcaggcc aaaattttta ctttcctttg aattttttcaa     600
```

```
ttcaaacaca atgtatgctt gcttttacac agtagggttc agggattaga gggttggctc    660
tttaaaaacc gtcagagaca caggcaatcc tacacaaaat tctcagaagg aaggcgccta    720
cgcctgggaa tgcccagatg cccctcagag agttgaagat ggcgtttctc tgagtcaggt    780
caaagttaac acattacctt cgcttcaaag actgcttggc ttcctttcgg tggattagtc    840
aagatgtttt gctgactgag actaggaaat ctataggagg gcgggttagt ttacattgtt    900
ccttgtcatt atcgctaaaa cactccaaag ccttccttaa aaatgcgcac tgggctaaaa    960
aggatagaca aggaacacat cctgggccgg taattacgca aagcattatc tcctcttacc   1020
tccttgcaga ttttttttc tctttcagta cgtgtcctaa gatttctgtg ccacccttgg    1080
agttcactca cctaaacctg aaactaataa agcttggttc ttttctccga cacgcaaagg   1140
aagcgctaag gtaaatgcat cagacccaca ctgccgcgga acttttcggc tctctaaggc   1200
tgtattttga tatacgaaag gcacattttc cttcccttt caaaatgcac cttgcaaacg    1260
taacaggaac ccgactagga tcatcgggaa aaggaggagg aggaggaagg caggctccgg   1320
ggaagctggt ggcagcgggt cctgggtctg gcggaccctg acgcgaagga gggtctagga   1380
agctctccgg ggagccggtt ctcccgccgg tggcttcttc tgtcctccag cgttgccaac   1440
tggacctaaa gagaggccgc gactgtcgcc cacctgcggg atgggcctgg tgctgggcgg   1500
taaggacacg gacctggaag gagcgcgcgc gagggaggga ggctggagt cagaatcggg    1560
aaagggaggt gcggggcggc gagggagcga aggaggagag gaggaaggag cgggaggggt   1620
gctggcgggg gtgcgtagtg ggtggagaaa gccgctagag caaatttggg gccggaccag   1680
gcagcactcg gcttttaacc tgggcagtga aggcggggga aagagcaaaa ggaaggggtg   1740
gtgtgcggag taggggtggg tgggggaat tggaagcaaa tgacatcaca gcaggtcaga    1800
gaaaaagggt tgagcggcag gcacccagag tagtaggtct ttggcattag gagcttgagc   1860
ccagacggcc ctagcaggga ccccagcgcc cgagagacca tgcagaggtc gcctctggaa   1920
aaggccagcg ttgtctccaa acttttttc aggtgagaag gtggcaacc gagcttcgga    1980
aagacacgtg cccacgaaag aggagggcgt gtgtatgggt tgggtttggg gtaaaggaat   2040
aagcagtttt taaaaagatg cgctatcatt cattgttttg aaagaaaatg tgggtattgt   2100
agaataaaac agaaagcatt aagaagagat ggaagaatga actgaagctg attgaataga   2160
gagccacatc tacttgcaac tgaaaagtta gaatctcaag actcaagtac gctactatgc   2220
acttgtttta tttcattttt ctaagaaact aaaaatactt gttaataagt acctaagtat   2280
ggtttattgg ttttccccct tcatgccttg gacacttgat tgtcttcttg gcacatacag   2340
gtgccatgcc tgcatatagt aagtgctcag aaaacatttc ttgactgaat tcagccaaca   2400
aaaattttgg ggtaggtaga aaatatatgc ttaaagtatt tattgttatg agactggata   2460
tatctagtat ttgtcacagg taaatgattc ttcaaaaatt                         2500

<210> SEQ ID NO 2
<211> LENGTH: 19
<212> TYPE: DNA
<213> ORGANISM: Homo sapiens

<400> SEQUENCE: 2 ggcggggtg cgtagtggg                                                    19

<210> SEQ ID NO 3
<211> LENGTH: 19
<212> TYPE: DNA
<213> ORGANISM: Homo sapiens
```

-continued

```
<400> SEQUENCE: 3
gcctgggcag tgaaggcgg                                              19

<210> SEQ ID NO 4
<211> LENGTH: 20
<212> TYPE: DNA
<213> ORGANISM: Homo sapiens

<400> SEQUENCE: 4
gaaagagcaa aaggaagggg                                             20

<210> SEQ ID NO 5
<211> LENGTH: 19
<212> TYPE: DNA
<213> ORGANISM: Homo sapiens

<400> SEQUENCE: 5
gtaaaggtac aaaacttac                                              19

<210> SEQ ID NO 6
<211> LENGTH: 21
<212> TYPE: DNA
<213> ORGANISM: Homo sapiens

<400> SEQUENCE: 6
ggccggacca ggcagcactc g                                           21
```